United States Patent
O'Lenick

(10) Patent No.: US 12,281,209 B1
(45) Date of Patent: Apr. 22, 2025

(54) POLYMER DISPERSED CELLULOSE NANOCRYSTALS

(71) Applicant: Thomas O'Lenick, Monroe, GA (US)

(72) Inventor: Thomas O'Lenick, Monroe, GA (US)

( * ) Notice: Subject to any disclaimer, the term of this patent is extended or adjusted under 35 U.S.C. 154(b) by 881 days.

(21) Appl. No.: 17/409,917

(22) Filed: Aug. 24, 2021

Related U.S. Application Data

(60) Provisional application No. 63/078,504, filed on Sep. 15, 2020.

(51) Int. Cl.
| | |
|---|---|
| C08J 3/02 | (2006.01) |
| A61K 8/73 | (2006.01) |
| A61K 8/85 | (2006.01) |
| A61Q 17/04 | (2006.01) |
| C08G 63/199 | (2006.01) |
| C08G 63/20 | (2006.01) |

(52) U.S. Cl.
CPC ............. *C08J 3/02* (2013.01); *A61K 8/731* (2013.01); *A61K 8/85* (2013.01); *A61Q 17/04* (2013.01); *C08G 63/199* (2013.01); *C08G 63/20* (2013.01); *A61K 2800/413* (2013.01); *C08J 2301/02* (2013.01); *C08J 2301/10* (2013.01); *C08J 2367/02* (2013.01); *C08L 2201/56* (2013.01)

(58) Field of Classification Search
None
See application file for complete search history.

(56) References Cited

U.S. PATENT DOCUMENTS 8,912,233 B1 * 12/2014 O'Lenick ................. A61K 8/85
514/574

OTHER PUBLICATIONS

Proposed Amendments to the claims (Year: 2024).*

* cited by examiner

*Primary Examiner* — Peter A Salamon

(57) ABSTRACT

The present invention relates to a dispersion of cellulosic nanocrystals (CNCs) that is capable of reflecting/scattering UV radiation. A very specific class of polyesters have found to be effective in making reflective dispersions that can range over a very wide range of radiation, including IR and UV. The resulting dispersion, when applied to the skin or surface, can provide protection from the UV rays of the sun.

10 Claims, 2 Drawing Sheets

POLYMER DISPERSED CELLULOSE NANOCRYSTALS

Government Sponsorship

None

RELATED APPLICATIONS

The present application claims the benefit of U.S. Provisional Application No. 63/078,504 filed Sep. 15, 2020, the entire contents of which are incorporated by reference.

FIELD OF THE INVENTION

The present invention is directed to a polymeric dispersions of cellulose nanocrystals (CNCs) that are easily dispersed in a polymer matrix, without the need to surface modify or the application of mechanical force. The polymer dispersion will have defined and controlled crystal size that can reflect ultraviolet (UV), visible (VIS) and infrared light (IR) depending upon the dispersion agent chosen. A polymer dispersion of this nature provides benefit in the personal care applications including but not limited to SPF protection in sun-care. Additionally, the dispersions are biodegradable, and are non-plastic film former. Along with several industrial applications including the incorporation of cellulose nanocrystals into concrete to provide better water transport.

BACKGROUND OF THE INVENTION

Cellulose is the most abundant natural polymer available on earth. George, J. teaches Naturally occurring bulk cellulose consists of highly ordered, crystalline regions (microfibrils) along with some disordered (amorphous) regions in varying proportions, depending on its source. When these microfibrils are subjected to a proper combination of mechanical, chemical, and enzyme treatments, the highly crystalline regions of the cellulose microfibrils can be extracted, resulting in the formation of cellulose nanocrystals (CNCs).

Cellulose nanocrystals, alternatively called nanowhiskers, are shorter than microfibrils and rod-like due to strong acid hydrolysis. Nanofibrillated cellulose is a remarkable emerging class of naturally derived nanomaterials for its extraordinary mechanical properties, combining astonishing stiffness and expected strength with a lightweight character, W. H. Kai, A. Isogai, T. Iwata, Biomacromolecules 2009, 10, 2571.

Cao, X et al. teaches us: The main challenge in achieving excellent performance lies in attaining homogeneous dispersion of nanocrystals within the polymer matrix and a good matrix-filler interaction. Good dispersibility of the CNCs in the polymer matrix is a prerequisite to make polymer nanocomposites with better properties, as a non-homogeneous dispersion of the filler in the polymer matrix decreases the final mechanical properties of the nanocomposite materials.

In polymer nanocomposite systems, attaining uniform dispersions and distribution of CNC in a polymer matrix is still a challenging issue. A tailor-made chemical modification process is necessary to incorporate CNCs into different polymer matrix systems effectively.

U.S. Pat. No. 8,912,233 to O'Lenick teaches us about a polyester synthesized utilizing propane diol. These polymers were used as film formers in cosmetic applications while providing a unique solubility and aesthetics. Surprisingly and unexpectantly, these polymers when used in a process defined herein, provide the dispersions of the current invention. The polyesters of '233 when used to disperse the properly selected cellulose nanocrystal, at 35% by weight under mechanical agitation, and were found to be stable and reflected UV light.

It is not until the present invention where polymer dispersed cellulose nanoparticles are easily dispersed in a polymer matrix without the need of a solvent or extraction agent. Furthermore, the polymer dispersion can reflect UV and visible light. Which makes them attractive in the personal care market in a wide variety of applications involving but not limited to: SPF boosting, hair dye protection, pigmented face products.

Natarajan, et. al. taught us that CNC films of two different surface functionalities when allowed to self-assemble from a water solution, can reflect/scatter visible light. In the current invention we have surprisingly found that when the cellulose described herein is dispersed in the polyesters herein described a surprisingly stable dispersion without the need of drying them down from a water solution. Furthermore, the dispersion will reflect and scatter UV as well as visible light, which is unforeseen until now. After drying CNCs from a water-based solution, the CNCs are extremely difficult to incorporate into other formulations, a CNC dispersion of the current invention allows for the CNCs to be incorporated into numerous formulations with relative ease.

Despite decades of work on safe and effective sun protection with absorbing UV filters which pass their energy on to DNA and results in DNA damage that increases the occurrence of cancer, the cellulose dispersion of the present invention reflects UV and no penetration and consequently no DNA damage. The dispersions of the present invention are not sun screen actives, rather they function by a completely different, non-absorbing mechanism. At last a safe and effective sun protectant has been developed.

All patents referenced are incorporated herein by reference. All percentages described are percentages by weight, all temperatures are degrees Celsius (C), unless otherwise states.

Sunscreens are products combining several ingredients that help prevent the sun's ultraviolet (UV) radiation from reaching the skin. Two types of ultraviolet radiation, UVA and UVB, damage the skin, age it prematurely, and increase your risk of skin cancer. UVB is the chief culprit behind sunburn, while UVA rays, which penetrate the skin more deeply, are associated with wrinkling, leathering, sagging, and other light-induced effects of aging (photoaging). They also exacerbate the carcinogenic effects of UVB rays, and increasingly are being seen as a cause of skin cancer on their own. Sunscreens vary in their ability to protect against UVA and UVB.

UV radiation is part of the electromagnetic (light) spectrum that reaches the earth from the sun. It has wavelengths shorter than visible light, making it invisible to the naked eye. These wavelengths are classified as UVA, UVB, or UVC, with UVA the longest of the three at 320-400 nanometers (nm, or billionths of a meter). UVA is further divided into two wave ranges, UVA I, which measures 340-400 nanometers (nm, or billionths of a meter), and UVA II which extends from 320-340 nanometers. UVB ranges from 290 to 320 nm. With even shorter rays, most UVC is absorbed by the ozone layer and does not reach the earth.

Both UVA and UVB, however, penetrate the atmosphere and play an important role in conditions such as premature skin aging, eye damage (including cataracts), and skin cancers. They also suppress the immune system, reducing your ability to fight off these and other maladies.

By damaging the skin's cellular DNA, excessive UV radiation produces genetic mutations that can lead to skin cancer. Both the U.S. Department of Health and Human Services and the World Health Organization have identified UV as a proven human carcinogen. UV radiation is considered the main cause of nonmelanoma skin cancers (NMSC), including basal cell carcinoma (BCC) and squamous cell carcinoma (SCC). These cancers strike more than a million and more than 250,000 Americans, respectively, each year. Many experts believe that, especially for fair-skinned people, UV radiation also frequently plays a key role in melanoma, the deadliest form of skin cancer, which kills more than 8,000 Americans each year.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

OBJECT OF THE INVENTION

It is one objective of this invention to provide polymer dispersed cellulose nanoparticles that are easily dispersed in a polymer matrix without the need of a solvent or extraction agent.

It is another objective of the present invention to provide a dispersion capable of reflecting/scattering UV radiation. When this dispersion is applied topically, it can provide protection of the skin from effects deleterious UV and visible light.

An additional aspect of the present invention is to provide the ability to dispersion topically as an additive to the personal care industry. Personal care products that are targeted are: sunscreen formulation, body washes, conditioners, and providing film formation with a naturally based biodegradable, non-plastic material.

SUMMARY OF THE INVENTION

In this context, the term "nanofibrillar cellulose" or "nanofibrillated cellulase" is used, it being understood that also "microfibrillar cellulose" or "nanocellulose" are commonly used terms for the substance to be described in more detail below.

The current invention provides a straightforward and simple way to create a polymeric dispersion of cellulose nanocrystals without the need for solvent or surface modification of the cellulose. The dispersion requires a particular polyester that surprisingly and unexpectantly has an ability to provide simple dispersions of many different types of cellulose as described that are stable and effective. Making dispersions of these cellulose products has been a long felt need and a major challenge, we have efficiently solved. Furthermore, these dispersions are capable of reflecting and/or scattering ultra-violet light.

Without wanting to be held to a specific mechanism, we have found that the selection of the different polyesters and dispersing the specific CNC's as describes herein together, the so-called "pitch angle" of the crystals can be altered and this in turn alters the wavelength of the reflected light, from IR to UV. One must clearly understand this mechanism is reflective, and is not based upon absorption. The latter process is much more damaging as photo instability will alter the wavelength and photo destabilize the standard UV absorbers.

DETAILED DESCRIPTION OF THE INVENTION

One aspect of the present invention is directed towards a cellulose nanocrystal dispersion made by the mixing of:
1. a cellulose nanocrystals dispersion which comprises:
   A. 0.1-12.0% by weight a functionalized cellulose selected from:
      a. sodium sulfate half ester,
      b. carboxylated,
      c. imidizolium salts
         1. hexyl, methyl,
         2. imidizolum chloride,
         3. phosphonium salts,
         4. ammonium salts.
      d. cellulose nano-fibers;
      e. plant based cellulose nano-crystals and mixtures thereof;

and
2. 88.0-99.9% by weight of a polyester made by the reaction of:
   A. a Guerbet alcohol having the following structure:

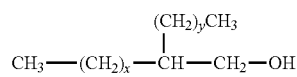

Wherein:
y is an integer ranging from 3-15;
x is an integer ranging from 5-17.
   B. 1,3 Propane diol having the following structure:

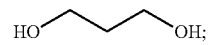

C. a diacid selected from the group consisting of
      a. dimer acid having the following structure:

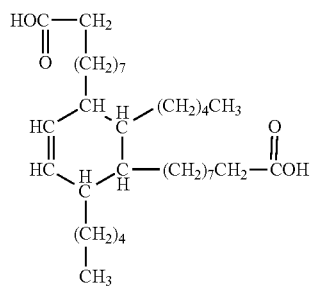

b. hydrogenated dimer acid having the following structure:

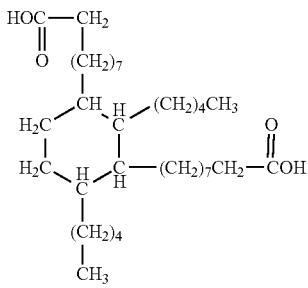

and mixtures thereof.

wherein the resulting dispersion reflects/scatters 240-400 nm light.

Another aspect of the present invention is directed towards a process for protecting skin from UV radiation which comprises contacting the skin with an effective UV reflecting or scattering dispersion of polymer dispersed cellulose nanocrystals prepared by mixing:

1. A cellulose nanocrystals dispersion which comprises:

A. A functionalized selected from:

c. sodium sulfate half ester, d. carboxylated, e. imidizolium salts 1. hexyl, methyl, 2. imidizolum chloride, 3. phosphonium salts, and 4. ammonium salts.

and mixtures thereof:

B. cellulose nano-fibers;

C. plant based cellulose nano-crystals and 3. a polyester made by the reaction of:

A. a Guerbet alcohol having the following structure:

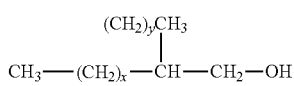

y is an integer ranging from 3-15;

and x is an integer ranging from 5-17.

B. 1,3 Propane diol having the following structure:

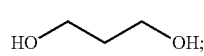

C. a diacid selected from the group consisting of
   a. dimer acid having the following structure:

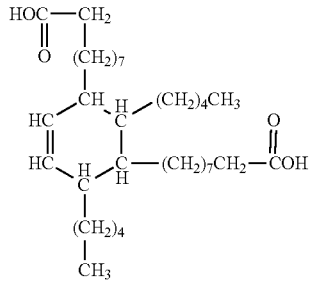

b. hydrogenated dimer acid having the following structure:

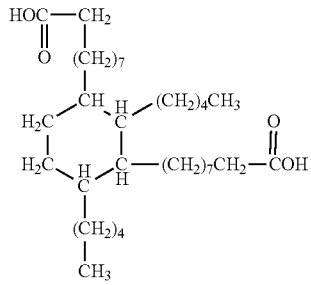

and mixtures thereof.

wherein the resulting dispersion reflects/scatters 240-400 nm light.

The amount of cellulose nanocrystal ranges from 0.1%-15.0% by weight and the polyester ranges from 85.0-99.9% by weight with 90.0% being the most desired.

The cellulose nanocrystal is added to the polyester and the liquid is mixed with an agitator until a homogeneous dispersion results. The mixture is surprisingly effective at reflecting and scattering different wavelengths of UV radiation.

Raw Materials

Cellulose Nanocrystals (CNCs)

There are many forms of cellulose that Wood based cellulose nanocrystals in the following functionalities: Sodium sulfate half ester functionalized, carboxylated (mostly via tempo oxidation).

Also tested were cellulose that was modified by Ion exchange with ionic liquids. This includes: imidizolium salts, 7 different ones that were derivatives of hexyl, methyl, imidizolum chloride, phosphonium salts, and ammonium salts.

Cellulose nano-fibers that have had lignin removed and nano fibers still containing lignin. These are produced mechanically and then treated with sodium hydroxide to remove the soluble lignin.

Tunicate produced cellulose nano-crystals: containing sodium sulfate half esters, These are very interesting due to their massive aspect ratio.

Plant based cellulose nano-crystals were also tried. The most common plant based nanocrystals are cotton cellulose, wheat grass, bamboo, M. gigantous (derivative of bamboo), and corn.

Cellulosic nano-crystals (CNCs) are commercially available from a variety of sources including CelluForce Inc. of Montreal, Quecec, Canada.

| Example | Type of Cellulose |
|---|---|
| 1 | Sodium sulfate half ester |
| 2 | Carboxylated |
| 3 | Imidizolium salts |
| 4 | Cellulose Nano-fibers |

Propanediol Polyester

The propanediol polyesters are commercially available from SurfaTech Corporation of Lawrenceville, Georgia.
   Trade Name: CosmoSurf® DDG 20
      INCI: Bis-Octyldodecyl Dimer Dilinoleate/Propanediol Copolymer
   CAS Numer: 1386384-61-4

| Example | Trade Name | INCI |
|---|---|---|
| 5 | CosmoSurf® DDG 20 | Bis-Octyldodecyl Dimer Dilinoleate/Propanediol Copolymer |
| 6 | CosmoSurf® DDG 28 | Bis-Dodecylhexadecyl Dimer Dilinoleate/Propanediol Copolymer |

| | CNCs | | Propanediol Polyesters | |
|---|---|---|---|---|
| Example | Example | Grams | Example | Grams |
| 7 | 1 | 0.1 | 5 | 99.9 |
| 8 | 1 | 1.0 | 5 | 99.0 |
| 9 | 1 | 3.0 | 5 | 97.0 |
| 10 | 1 | 5.0 | 5 | 95.0 |
| 11 | 1 | 10.0 | 5 | 90.0 |
| 12 | 1 | 12.0 | 5 | 88.0 |
| 13 | 2 | 0.1 | 5 | 99.9 |
| 14 | 2 | 3.0 | 5 | 97.0 |
| 15 | 2 | 5.0 | 5 | 95.0 |
| 16 | 2 | 12.0 | 5 | 88.0 |
| 17 | 3 | 0.1 | 5 | 99.9 |
| 18 | 3 | 3.0 | 5 | 97.0 |
| 19 | 3 | 5.0 | 5 | 95.0 |
| 20 | 3 | 12.0 | 5 | 88.0 |
| 21 | 4 | 0.1 | 5 | 99.9 |
| 22 | 4 | 3.0 | 5 | 97.0 |
| 23 | 4 | 5.0 | 5 | 95.0 |
| 24 | 4 | 12.0 | 5 | 88.0 |
| 25 | 1 | 0.1 | 6 | 99.9 |
| 26 | 1 | 1.0 | 6 | 99.0 |
| 27 | 1 | 3.0 | 6 | 97.0 |
| 28 | 1 | 5.0 | 6 | 95.0 |
| 29 | 1 | 12.0 | 6 | 88.0 |
| 30 | 2 | 0.1 | 6 | 99.9 |
| 31 | 2 | 3.0 | 6 | 97.0 |
| 32 | 2 | 5.0 | 6 | 95.0 |
| 33 | 2 | 12.0 | 6 | 88.0 |
| 34 | 3 | 0.1 | 6 | 99.9 |
| 35 | 3 | 3.0 | 6 | 97.0 |
| 36 | 3 | 5.0 | 6 | 95.0 |
| 37 | 3 | 12.0 | 6 | 88.0 |
| 38 | 4 | 0.1 | 6 | 99.9 |
| 39 | 4 | 3.0 | 6 | 97.0 |
| 40 | 4 | 5.0 | 6 | 95.0 |
| 41 | 4 | 12.0 | 6 | 88.0 |

Dispersion Procedure

A specific amount of propanediol polyester (examples 5-7) are added into a container. CNCs are added into the container (example 1-4) and the container and shear mixed using a speed mixer for 10 minutes. A highly viscous transparent fluid was obtained.

Procedure for UV-Vis

The dispersion was sandwiched between two cover slips and placed in a solid-state holder. The absorbance of the propane diol polyesters with sodium sulfate functionalized cellulose nanocrystals were measured on a Shimatzu UV-VIS in the range of 250-800 nm.

| | CNCs | | Propanediol Polyesters | |
|---|---|---|---|---|
| Example | Example | Grams | Example | Grams |
| 8 | 1 | 1.0 | 5 | 99.0 |
| 9 | 1 | 3.0 | 5 | 97.0 |
| 10 | 1 | 5.0 | 5 | 95.0 |
| 11 | 1 | 10.0 | 5 | 90.0 |
| 26 | 1 | 1.0 | 6 | 99.0 |
| 27 | 1 | 3.0 | 6 | 97.0 |
| 28 | 1 | 5.0 | 6 | 95.0 |
| 29 | 1 | 12.0 | 6 | 88.0 |

Comparison with Another Dispersant Agent

CNCs were also dispersed with a commercially available dispersant agent, poly(hydroxystearic acid), and the UV spectrum was obtained. Poly(hydroxystearic Acid) is the most commonly used as a dispersing agent for inorganic particles for suncare. Poly(hydroxystearic acid) was capable of dispersing the CNCs, as seen in the UV spectrum, the dispersion was not capable of scattering/refection UV light.

| | Dispersing Agent | | CNC | |
|---|---|---|---|---|
| Example | Name | Grams | Example | Grams |
| 30 | Example 5 | 97.0 | 2 | 3.0 |
| 31 | Example 6 | 97.0 | 2 | 3.0 |
| 32 | Poly(hydroxystearic acid) | 97.0 | 2 | 3.0 |

DETAILED DESCRIPTION OF THE DRAWINGS

Figure 1:
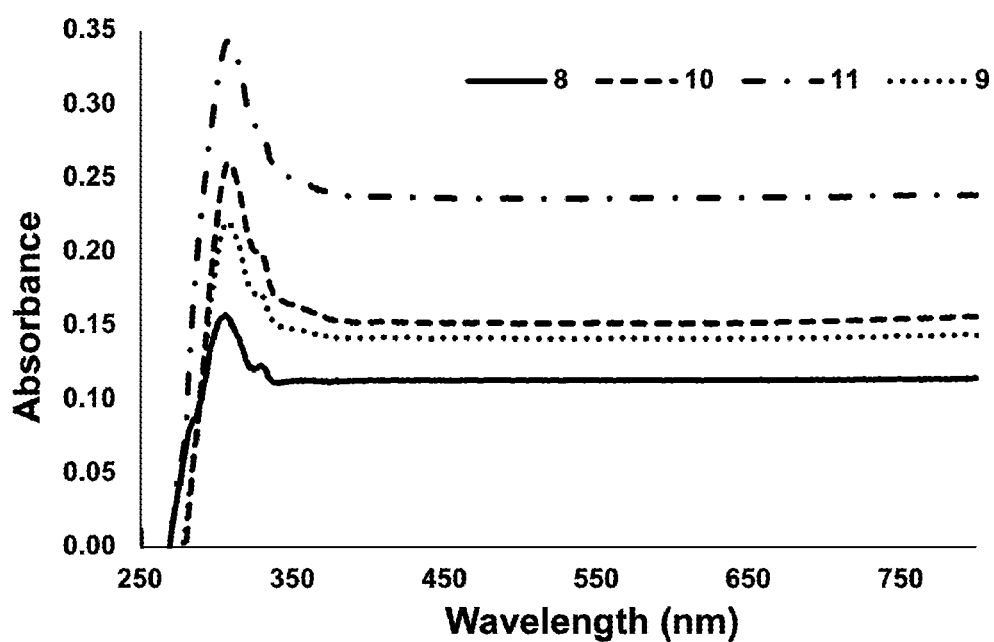
FIG. 1 is a line graph showing the absorption versus wavelength of examples 8-11. The absorbance is plotted on the y-axis and wavelength in nanometers is plotted on the x-axis.

FIG. 1 shows the absorption spectra of examples 8-11 taken on a Shimatzu UV-VIS instrument. The figure shows a strong absorbance from 280-800 nm for examples 8-11. The figure also shows that the more CNCs in the dispersion, the higher the absorption.

Figure 2:
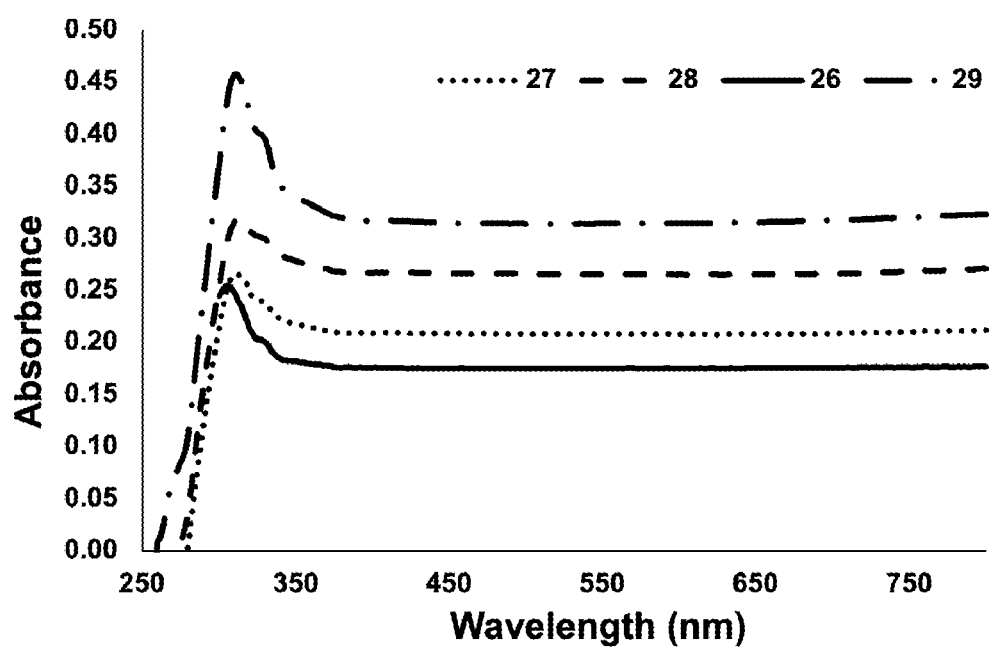
FIG. 2 is a line graph showing the absorption versus wavelength of examples 26-29. The absorbance is plotted on the y-axis and wavelength in nanometers is plotted on the x-axis.

FIG. 2 shows the absorption versus wavelength of examples 26-29 taken on a Shimatzu UV-VIS instrument. The figure shows a strong absorbance from 280-800 nm with the strongest absorption occurring at 306 nm. FIG. 2 also shows that the absorption increases as the amount of CNCs is increased.

Figure 3:
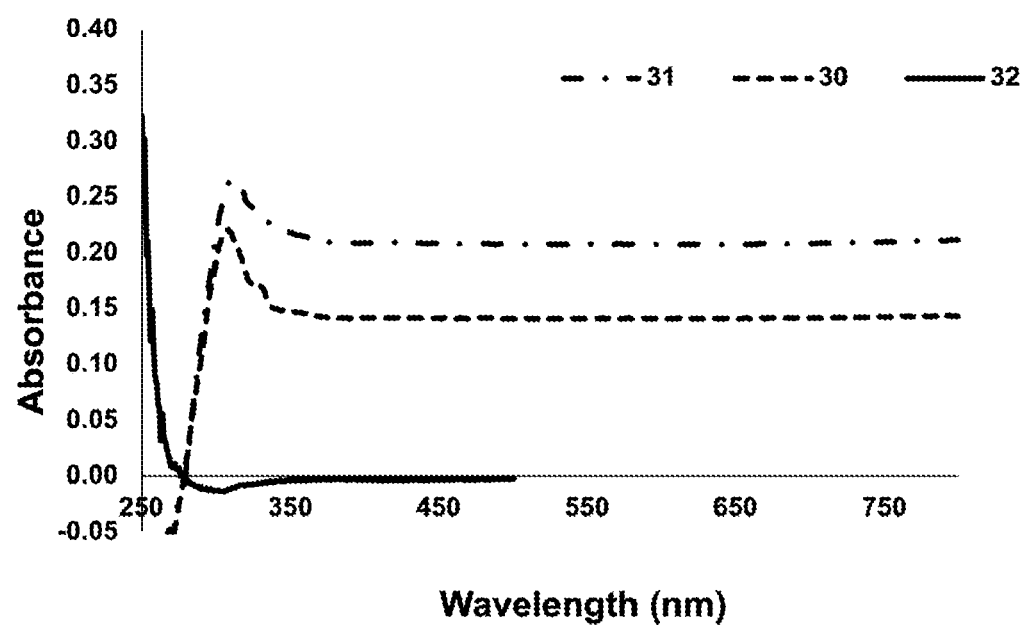
FIG. 3 is a line graph showing the absorption versus wavelength of examples 30-32 and poly(hydroxystearic acid). The absorbance is plotted on the y-axis and wavelength in nanometers is plotted on the x-axis.

FIG. 3 shows the absorption versus wavelength of examples 30-32 taken on a Shimatzu UV-VIS instrument. The figure shows a strong absorbance from 280-800 nm with the strongest absorption occurring at 306 nm. Also shown in the figure is a comparison of the dispersions of the current invention and the most commonly used dispersion agent in the personal care market, poly(hydroxy stearic acid). As seen in the figure, the dispersion of the current invention surprisingly and unexpectedly has a absorption from 280 nm to 800 nm, meanwhile the absorption of the dispersion in poly(hydroxy stearic acid) show an absorption at 250 nm, but a zero absorption from 280 nm to 500 nm.

The invention claimed is:

1. A cellulose nanocrystal dispersion comprising:
    a. 0.1 to 12% wt/wt of cellulose nanocrystals selected from the group consisting of cellulose nanocrystals functionalized with the following; sodium sulfate half ester, carboxylated, imidazolium salts; hexyl imidazolium salts, methyl imidazolium salts, imidazolium salts, imidazolium chloride, phosphonium salts, ammonium salts, cellulose nano-fibers and plant based cellulose, cellulose nano-fibers, and plant based cellulose nanocrystals and mixtures thereof;
    and
    b. 88.0-99.9% by weight of a polyester made by the reaction of:
        1. Guerbet alcohol having the following structure:

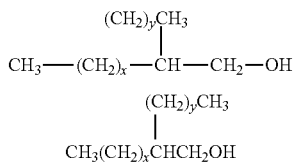

y is an integer ranging from 3-15;
x is an integer ranging from 5-17;
        2. 1,3 propanediol having the following structure:

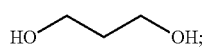

3. a diacid selected from the group consisting of:

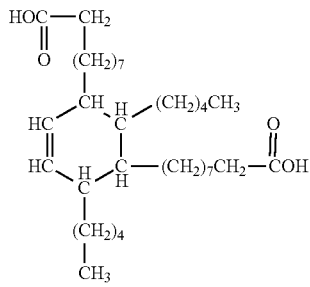

and a hydrogenated dimer acid having the following structure:

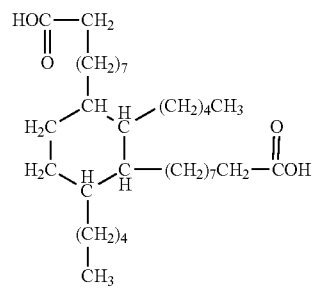

and
mixtures thereof,
wherein the resulting dispersion reflects/scatters 240-400 nm light.

2. A cellulose nanocrystal dispersion of claim 1, which comprises between 0.1 to 12% by weight sodium sulfate half ester CNCs with a polyester where in: x is 9, y is 7, and diacid is hydrogenated dimer acid.

3. A cellulose nanocrystal dispersion of claim 1, which comprises between 0.1 to 12% by weight sodium sulfate half ester CNCs with a polyester where in: x is 13, y is 11, and diacid is hydrogenated dimer acid.

4. A cellulose nanocrystal dispersion of claim 1, which comprises between 0.1 to 12% by weight of plant based cellulose nano-crystals with a polyester where in: x is 9, y is 7, and diacid is hydrogenated dimer acid.

5. A cellulose nanocrystal dispersion of claim 1, which comprises between 0.1 to 12% by weight of plant based cellulose nano-crystals with a polyester where in: x is 13, y is 11, and diacid is hydrogenated dimer acid.

6. A process for protecting skin from UV radiation which comprises contacting skin with an effective UV reflecting or scattering dispersion of polymer dispersed cellulose nanocrystals prepared by mixing:
    a. a cellulose nanocrystal selected from the group consisting of cellulose nanocrystals functionalized with the following: sodium sulfate half ester, carboxylated, imidazolium salts, hexyl imidazolium salts, methyl imidazolium salts, imidizolum chloride, phosphonium salts, ammonium salts, cellulose nano-fibers and plant based cellulose nano-crystals and mixtures thereof; and
    b. a polyester made by the reaction of:
        1. a Guerbet alcohol having the following structure:

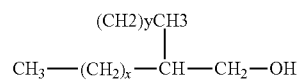

wherein:
y is an integer ranging from 3-15; x is an integer ranging from 5-17; and mixtures thereof; and 2. a propane diol having the following structure:

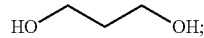

3. a diacid selected from the group consisting of:

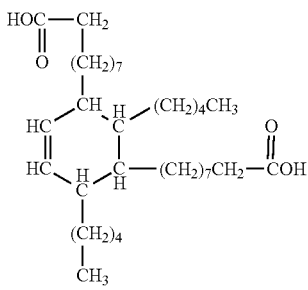

and a hydrogenated dimer acid having the following structure:

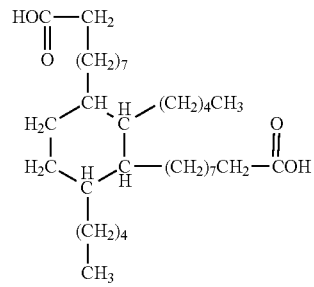

and mixtures thereof.

7. A process of claim 6, which comprises between 0. 1 to 12.0% by weight of sodium sulfate half ester CNCs with a polyester wherein: x is 9 and y is 7, and diacid is hydrogenated dimer acid.

8. A process of claim 6, which comprises between 0. 1 to 12.0% by weight of sodium sulfate half ester CNCs with a polyester wherein: x is 13 and y is 11, and diacid is hydrogenated dimer acid.

9. A process of claim 6, which comprises between 0.1 to 12.0% by weight of plant based cellulose nano-crystals with a polyester wherein: x is 9 and y is 7, and diacid is hydrogenated dimer acid.

10. A process of claim 6, which comprises between 0.1 to 12.0% by weight of plant based cellulose nano-crystals with a polyester wherein: x is 13 and y is 11, and diacid is hydrogenated dimer acid.

* * * * *